(12) United States Patent
Michihata et al.

(10) Patent No.: US 10,918,269 B2
(45) Date of Patent: Feb. 16, 2021

(54) MEDICAL LIGHT SOURCE APPARATUS AND MEDICAL OBSERVATION SYSTEM

(71) Applicant: Sony Olympus Medical Solutions Inc., Tokyo (JP)

(72) Inventors: Taihei Michihata, Kanagawa (JP); Kiminori Sugisaki, Kanagawa (JP); Yoichiro Sakanoue, Tokyo (JP); Koji Kojima, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/729,516

(22) Filed: Dec. 30, 2019

(65) Prior Publication Data

US 2020/0260939 A1    Aug. 20, 2020

(30) Foreign Application Priority Data

Feb. 18, 2019  (JP) .............................. JP2019-026888

(51) Int. Cl.
*A61B 1/04* (2006.01)
*H05B 45/32* (2020.01)
*H04N 5/235* (2006.01)
*A61B 1/06* (2006.01)
*A61B 1/00* (2006.01)
*H04N 5/225* (2006.01)

(52) U.S. Cl.
CPC ............ *A61B 1/043* (2013.01); *A61B 1/0002* (2013.01); *A61B 1/0638* (2013.01); *A61B 1/0684* (2013.01); *H04N 5/2256* (2013.01); *H04N 5/2354* (2013.01); *H05B 45/32* (2020.01); *H04N 2005/2255* (2013.01)

(58) Field of Classification Search
CPC ..... A61B 1/043; A61B 1/0002; A61B 1/0638; A61B 1/0684; H05B 45/32; H04N 5/2256; H04N 5/2354; H04N 2005/2255
USPC ......................................................... 348/68
See application file for complete search history.

(56) References Cited

U.S. PATENT DOCUMENTS

2005/0231739 A1*  10/2005  Lee .................... H04N 1/00278
                                               358/1.1
2017/0167980 A1*   6/2017  Dimitriadis ........ G01N 21/6428
2018/0234603 A1*   8/2018  Moore .................. H04N 5/332

FOREIGN PATENT DOCUMENTS

JP         2013-102899 A      5/2013

* cited by examiner

*Primary Examiner* — Joseph G Ustaris
*Assistant Examiner* — Matthew David Kim
(74) *Attorney, Agent, or Firm* — Xsensus LLP (57) ABSTRACT

A medical light source apparatus includes: a first light source configured to emit light in a first wavelength range; a second light source configured to emit light in a second wavelength range different from the first wavelength range; and a light source controller configured to control the first light source and the second light source to perform pulse light emission in a state in which the pulse light emission of the second light source is less frequent than the pulse light emission of the first light source.

9 Claims, 5 Drawing Sheets

FIG.4

MEDICAL LIGHT SOURCE APPARATUS AND MEDICAL OBSERVATION SYSTEM

This application claims priority from Japanese Application No. 2019-026888, filed on Feb. 18, 2019, the contents of which are incorporated by reference herein in its entirety.

BACKGROUND

The present disclosure relates to a medical light source apparatus and a medical observation system.

In the related art, a configuration in which a medical light source apparatus including first and second light sources is mounted in a medical observation system that captures an image of (observes) the inside of a living body (observation target) that is a subject has been known (for example, see JP 2013-102899 A).

In the medical light source apparatus described in JP 2013-102899 A, the first light source emits white light. On the other hand, the second light source emits excitation light that excites a fluorescent substance contained in the living body. In the medical light source apparatus, the first and second light sources alternately emit light in a time division manner.

SUMMARY

In the medical light source apparatus described in JP 2013-102899 A, it is assumed that there is a large difference in lifetime between the first and second light sources. For example, in a case where the first light source is implemented by a light emitting diode (LED) and the second light source is implemented by a semiconductor laser, the first light source has a longer lifetime than that of the second light source.

In the above-described case, since the first and second light sources alternately emit light in the medical light source apparatus described in JP 2013-102899 A in a time division manner, a usage time of the first light source is substantially the same as that of the second light source. Therefore, the second light source needs to be replaced due to lifetime expiration sooner than the first light source. That is, in a case of the configuration in which the first and second light sources are replaced substantially at the same time, it is possible to improve convenience. However, the replacement times of the first and second light sources are different from each other, and thus the convenience may not be improved, which is problematic.

There is a need for a medical light source apparatus and a medical observation system which may improve convenience.

According to one aspect of the present disclosure, there is provided a medical light source apparatus including: a first light source configured to emit light in a first wavelength range; a second light source configured to emit light in a second wavelength range different from the first wavelength range; and a light source controller configured to control the first light source and the second light source to perform pulse light emission in a state in which the pulse light emission of the second light source is less frequent than the pulse light emission of the first light source.

DETAILED DESCRIPTION

Hereinafter, embodiments for carrying out the present disclosure (hereinafter, referred to as embodiments) will be described with reference to the drawings. Note that the present disclosure is not limited to the embodiments described below. Furthermore, the same reference numeral denotes the same component in the description of the drawings.

Schematic Configuration of Medical Observation System

Figure 1:
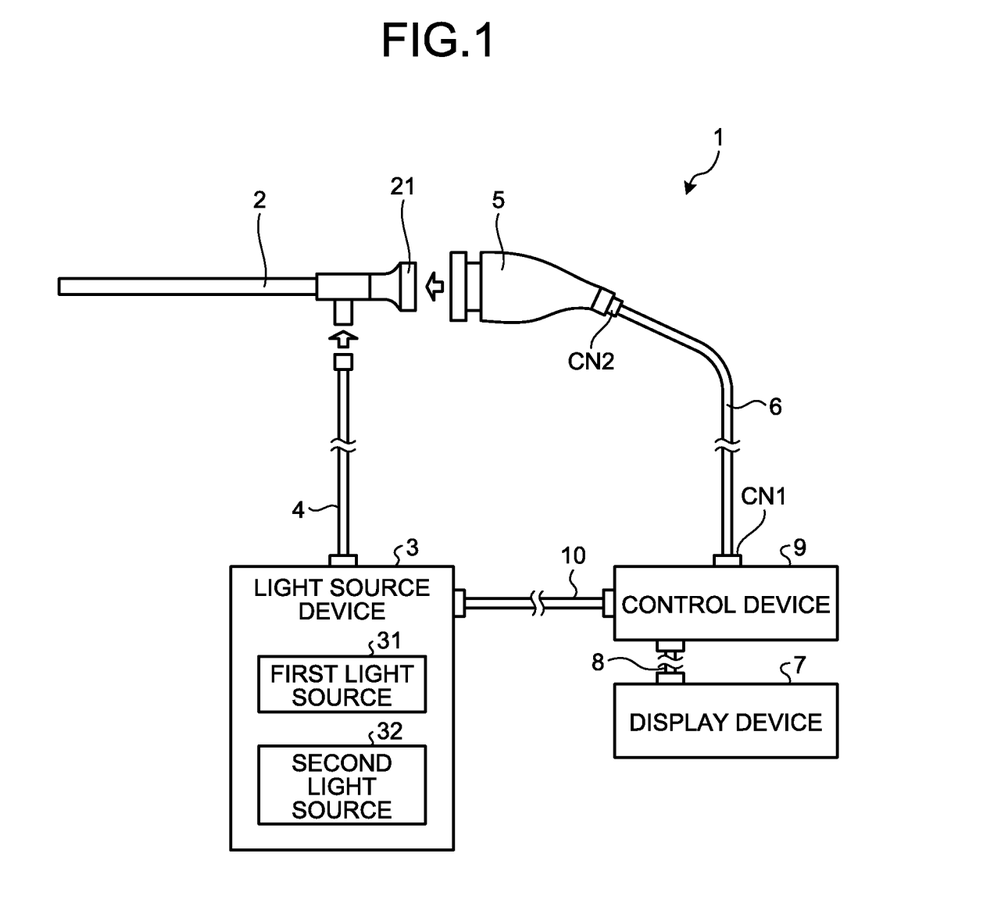
FIG. 1 is a diagram illustrating a configuration of a medical observation system according to an embodiment.

FIG. 1 is a diagram illustrating a configuration of a medical observation system 1 according to the present embodiment.

The medical observation system 1 is a system that is used in the medical field and captures an image of (observes) the inside of a living body (observation target) that is a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the present embodiment, the insertion unit 2 is implemented by a rigid endoscope. That is, the insertion unit 2 has an elongated shape that is entirely rigid, or is partially soft and partially rigid, and is inserted into the living body. An optical system configured by using one or a plurality of lenses and collecting light (subject image or fluorescent image) from the subject is provided in the insertion unit 2.

The light source device 3 is connected to one end of the light guide 4 and supplies, to one end of the light guide 4, light with which the inside of the living body is irradiated under the control of the control device 9. As illustrated in FIG. 1, the light source device 3 includes a first light source 31 and a second light source 32.

The first light source 31 emits light in a first wavelength range. In the present embodiment, the first light source 31 is implemented by a light emitting diode (LED) that emits white light.

The second light source 32 emits light in a second wavelength range different from the first wavelength range. In the present embodiment, the second light source 32 is implemented by a semiconductor laser that emits near-infrared excitation light in a near-infrared wavelength range. The near-infrared excitation light is excitation light that excites a fluorescent substance such as indocyanine green.

Then, in the light source device 3, the first light source 31 and the second light source 32 emit light in a first period T1 (see FIG. 4) and a second period T2, respectively, among the respective periods T (see FIG. 4) that are periodically repeated under the control of the control device 9, and this will be described later in detail.

Note that although the light source device 3 is configured separately from the control device 9 in the present embodiment, the present disclosure is not limited thereto, and a configuration in which the light source device 3 is provided inside the control device 9 may also be employed.

The light guide 4 has one end detachably connected to the light source device 3, and the other end detachably connected to the insertion unit 2. The light guide 4 transfers light (white light or near-infrared excitation light) supplied from the light source device 3 from one end to the other end and supplies the light to the insertion unit 2. The light supplied to the insertion unit 2 is emitted from a distal end of the insertion unit 2 and the inside of the living body is irradiated with the light. When the inside of the living body is irradiated with white light, the subject image reflected in the living body is collected by the optical system in the insertion unit 2. In addition, in a case where the inside of the living body is irradiated with near-infrared excitation light, a fluorescent substance (drug), such as indocyanine green, that accumulates in a lesion in the living body is excited, and a fluorescent image emitted from the inside of the living body is collected by the optical system in the insertion unit 2.

The camera head 5 corresponds to an imaging device according to the present disclosure. The camera head 5 is detachably connected to a proximal end (an eyepiece 21 (FIG. 1)) of the insertion unit 2. Then, under the control of the control device 9, the camera head 5 captures the subject image or the fluorescent image collected by the insertion unit 2, and outputs an image signal (RAW signal) obtained by the capturing. The image signal is, for example, an image signal of 4K or more.

A detailed configuration of the camera head 5 will be described later.

The first transmission cable 6 has one end detachably connected to the control device 9 via a connector CN1 (FIG. 1) and the other end detachably connected to the camera head 5 via a connector CN2 (FIG. 1). The first transmission cable 6 transmits an image signal and the like output from the camera head 5 to the control device 9, and transmits a control signal, a synchronization signal, a clock, power, and the like output from the control device 9 to the camera head 5.

Note that the transmission of the image signal or the like from the camera head 5 to the control device 9 via the first transmission cable 6 may be performed by transmitting the image signal or the like as an optical signal or by transmitting the image signal or the like as an electric signal. The same applies to transmission of a control signal, a synchronization signal, and a clock from the control device 9 to the camera head 5 via the first transmission cable 6.

The display device 7 is implemented by a display using liquid crystal, organic electro luminescence (EL), or the like, and displays an image based on a video signal from the control device 9 under the control of the control device 9.

The second transmission cable 8 has one end detachably connected to the display device 7 and the other end detachably connected to the control device 9. The second transmission cable 8 transmits the video signal processed by the control device 9 to the display device 7.

The control device 9 includes a central processing unit (CPU), a field-programmable gate array (FPGA), and the like, and controls general operations of the light source device 3, the camera head 5, and the display device 7.

A detailed configuration of the control device 9 will be described later.

The third transmission cable 10 has one end detachably connected to the light source device 3, and the other end detachably connected to the control device 9. The third transmission cable 10 transmits a control signal from the control device 9 to the light source device 3.

Configuration of Camera Head

Next, the configuration of the camera head 5 will be described.

Figure 2:
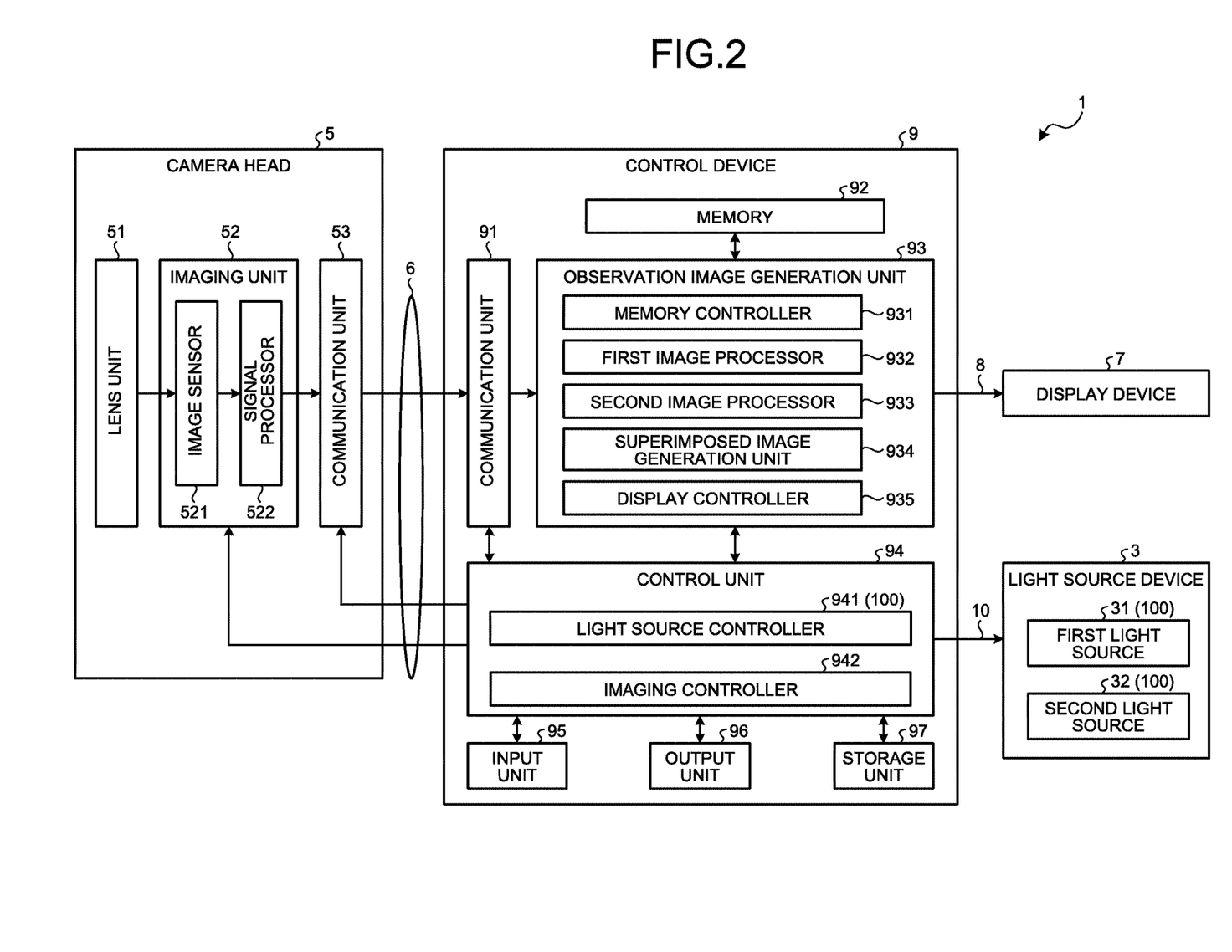
FIG. 2 is a block diagram illustrating a configuration of a camera head and a control device.

FIG. 2 is a block diagram illustrating a configuration of the camera head 5 and the control device 9.

For convenience of explanation, the connectors CN1 and CN2 between the control device 9 and the camera head 5, and the first transmission cable 6, connectors between the control device 9 and the display device 7, and the second transmission cable 8, and connectors between the control device 9 and the light source device 3, and the third transmission cable 10 are omitted in FIG. 2.

As illustrated in FIG. 2, the camera head 5 includes a lens unit 51, an imaging unit 52, and a communication unit 53.

The lens unit 51 is configured by using one or a plurality of lenses, and forms the subject image or the fluorescent image collected by the insertion unit 2 on an imaging surface of the imaging unit 52 (image sensor 521).

The imaging unit 52 captures an image of the inside of the living body under the control of the control device 9. As illustrated in FIG. 2, the imaging unit 52 includes the image sensor 521 and a signal processor 522.

The image sensor 521 is implemented by a charge coupled device (CCD) or a complementary metal oxide semiconductor (CMOS) that receives the subject image or the fluorescent image formed by the lens unit 51 and converts the subject image or the fluorescent image into an electric signal (analog signal). The image sensor 521 captures an image in each period T (see FIG. 4) that is periodically repeated, in synchronization with a light emission timing of the light source device 3 under the control of the control device 9. Hereinafter, for convenience of explanation, an image generated by capturing in the first period T1 by the image sensor 521 is referred to as a subject picture image (corresponding to a first captured image according to the present disclosure), and an image generated by capturing in the second period T2 by the image sensor 521 is referred to as a fluorescent picture image (corresponding to a second captured image according to the present disclosure). Further, the subject picture image and the fluorescent picture image are collectively referred to as a captured image.

The signal processor 522 performs signal processing on the captured image (analog signal) generated by the image sensor 521 and outputs the captured image (RAW signal (digital signal)).

The communication unit 53 functions as a transmitter that transmits the captured image (RAW signal (digital signal)) output from the imaging unit 52 to the control device 9 via the first transmission cable 6. The communication unit 53 is implemented by, for example, a high-speed serial interface that performs communication of the captured image with the control device 9 via the first transmission cable 6 at a transmission rate of 1 Gbps or more.

Configuration of Control Device

Next, the configuration of the control device 9 will be described with reference to FIG. 2.

As illustrated in FIG. 2, the control device 9 includes a communication unit 91, a memory 92, an observation image generation unit 93, a control unit 94, an input unit 95, an output unit 96, and a storage unit 97.

The communication unit 91 functions as a receiver that receives the captured image (RAW signal (digital signal)) output from the camera head 5 (communication unit 53) via the first transmission cable 6. For example, the communication unit 91 is implemented by a high-speed serial interface that performs communication of the captured image with the communication unit 53 at a transmission rate of 1 Gbps or more.

The memory 92 is implemented by a dynamic random access memory (DRAM) or the like. The memory 92 may temporarily store a plurality of frames of captured image output sequentially from the camera head 5 (communication unit 53).

The observation image generation unit 93 processes the captured image (RAW signal (digital signal)) sequentially output from the camera head 5 (communication unit 53) and received by the communication unit 91 under the control of the control unit 94. As illustrated in FIG. 2, the observation image generation unit 93 includes a memory controller 931, a first image processor 932, a second image processor 933, a superimposed image generation unit 934, and a display controller 935.

The memory controller 931 controls writing of the captured image to the memory 92 and reading of the captured image from the memory 92. More specifically, the memory controller 931 sequentially writes, to the memory 92, the captured images (the subject picture images and the fluorescent picture images) that are sequentially output from the camera head 5 (communication unit 53) and received by the communication unit 91. In addition, the memory controller 931 reads the subject picture image from the memory 92 at a specific timing, and inputs the read subject picture image to the first image processor 932. Further, the memory controller 931 reads the fluorescent picture image from the memory 92 at a specific timing, and inputs the read fluorescent picture image to the second image processor 933.

The first image processor 932 performs first image processing on the input subject picture image (RAW signal (digital signal)).

Examples of the first image processing may include optical black subtraction processing, white balance adjustment processing, demosaic processing, color correction processing, gamma correction processing, and YC processing of converting an RGB signal (first captured image) into a luminance signal and a color difference signal (Y, $C_B/C_R$ signal).

The second image processor 933 performs second image processing different from the first image processing on the input fluorescent picture image (RAW signal (digital signal)).

Examples of the second image processing may include processing of generating only a luminance signal (Y signal) from the input fluorescent picture image (RAW signal (digital signal)), and highlighting processing of discriminating a pixel position (a pixel position where a fluorescent substance such as indocyanine green is excited) where a luminance value is equal to or greater than a specific threshold in the entire image region from another pixel position.

The superimposed image generation unit 934 generates a superimposed image by superimposing corresponding regions (pixels) in entire regions of the subject picture image after the first image processing is performed by the first image processor 932 and the fluorescent picture image after the second image processing is performed by the second image processor 933.

The display controller 935 generates a video signal for display on the basis of the superimposed image generated by the superimposed image generation unit 934 under the control of the control unit 94. Then, the display controller 935 outputs the video signal to the display device 7 via the second transmission cable 8.

The control unit 94 is implemented by using a CPU, an FPGA, and the like, and outputs a control signal via the first to third transmission cables 6, 8, and 10 to control the operations of the light source device 3, the camera head 5, and the display device 7 and control the general operation of the control device 9. As illustrated in FIG. 2, the control unit 94 includes a light source controller 941 and an imaging controller 942. The light source controller 941 and the first and second light sources 31 and 32 correspond to a medical light source apparatus 100 (FIG. 2) according to the present disclosure. Functions of the light source controller 941 and the imaging controller 942 will be described in "Operation of Control Device" as described later.

The input unit 95 is implemented by an operation device such as a mouse, a keyboard, or a touch panel, and receives a user operation by a user such as a doctor. The input unit 95 outputs an operation signal corresponding to the user operation to the control unit 94.

The output unit 96 is implemented by a speaker, a printer, or the like, and outputs various information.

The storage unit 97 stores a program executed by the control unit 94, information necessary for processing performed by the control unit 94, and the like.

Operation of Control Device

Next, the operation of the control device 9 described above will be described.

Figure 3:
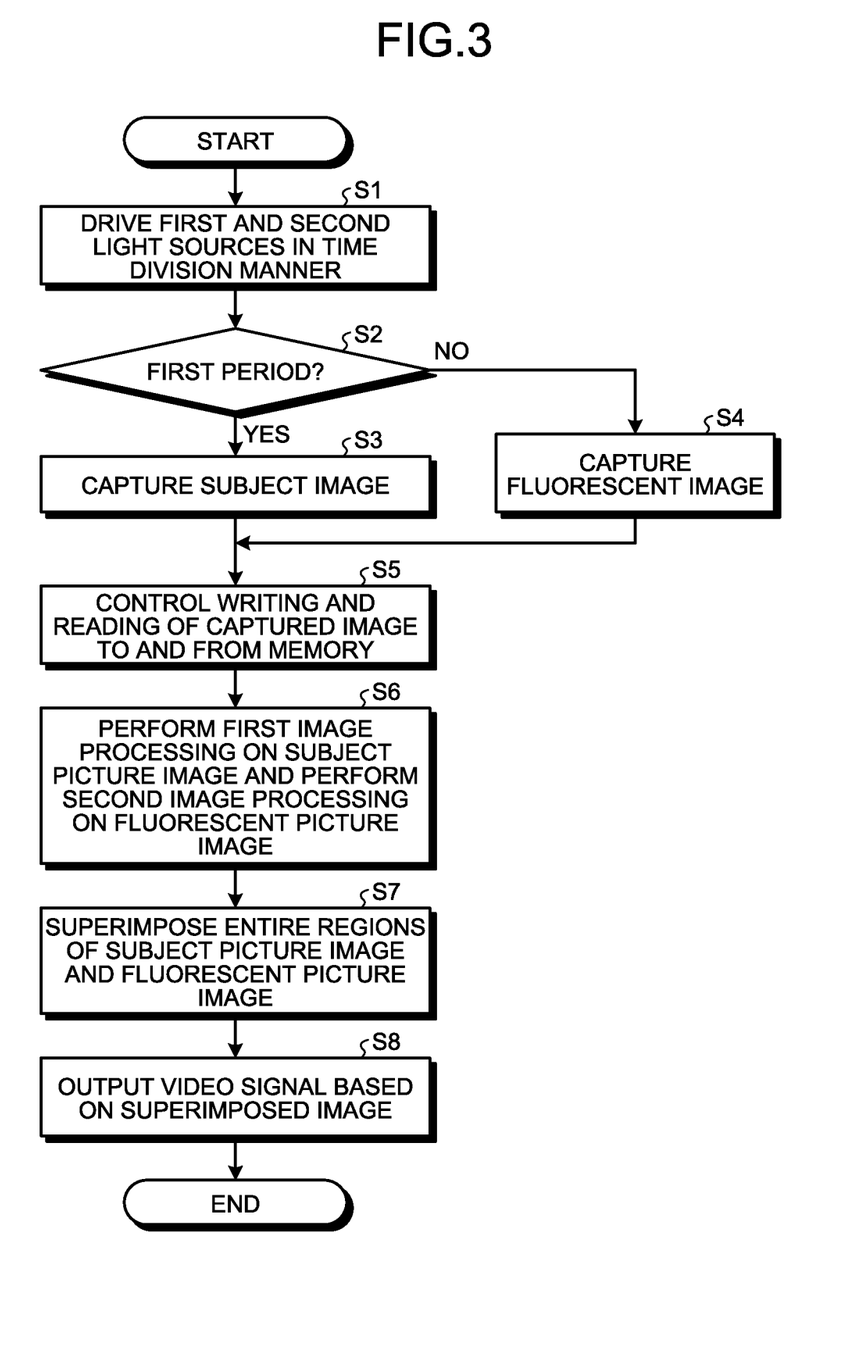
FIG. 3 is a flowchart illustrating operation of the control device.
Figure 4:
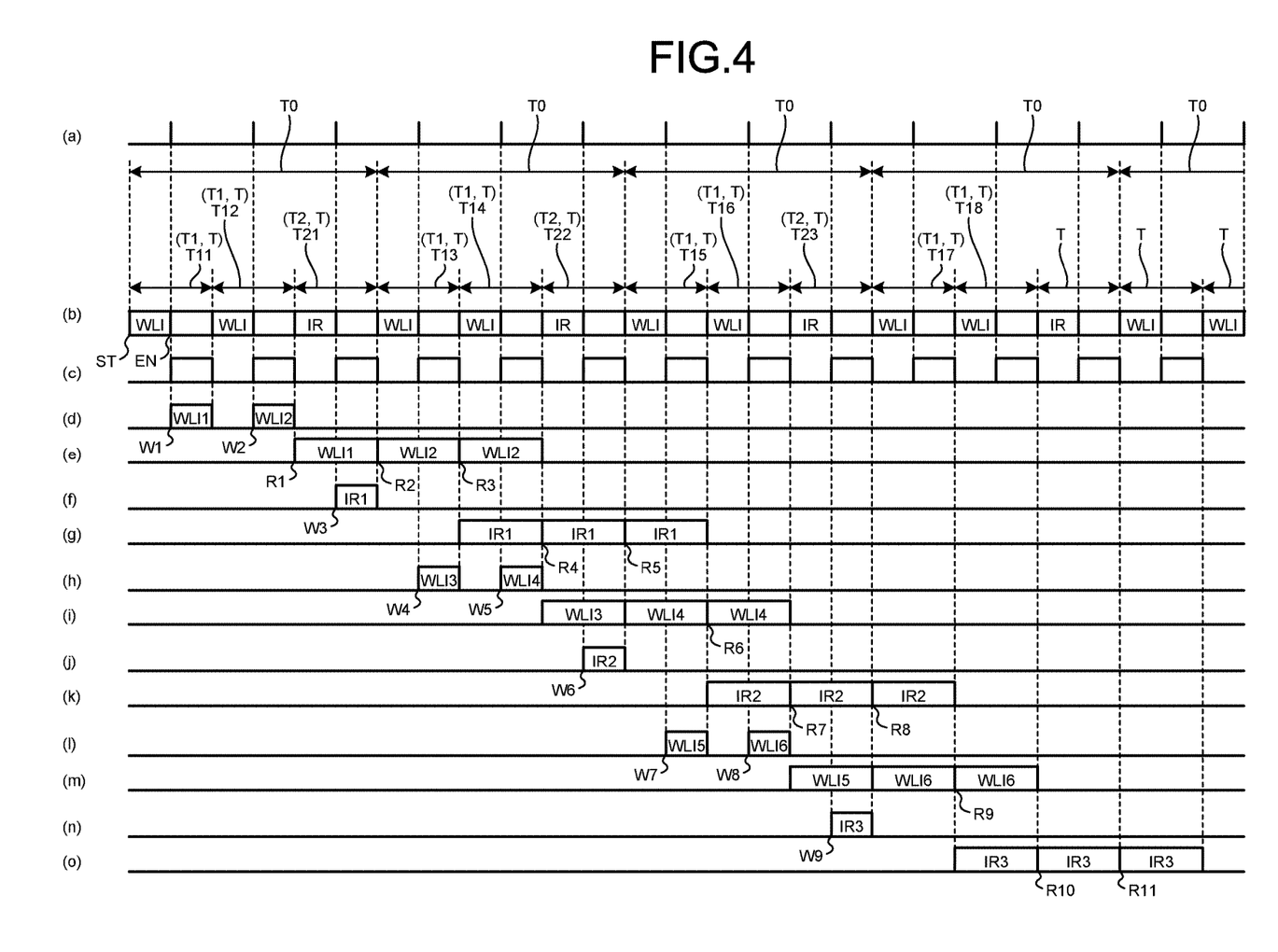
FIG. 4 is a diagram for describing the operation of the control device.
Figure 5:
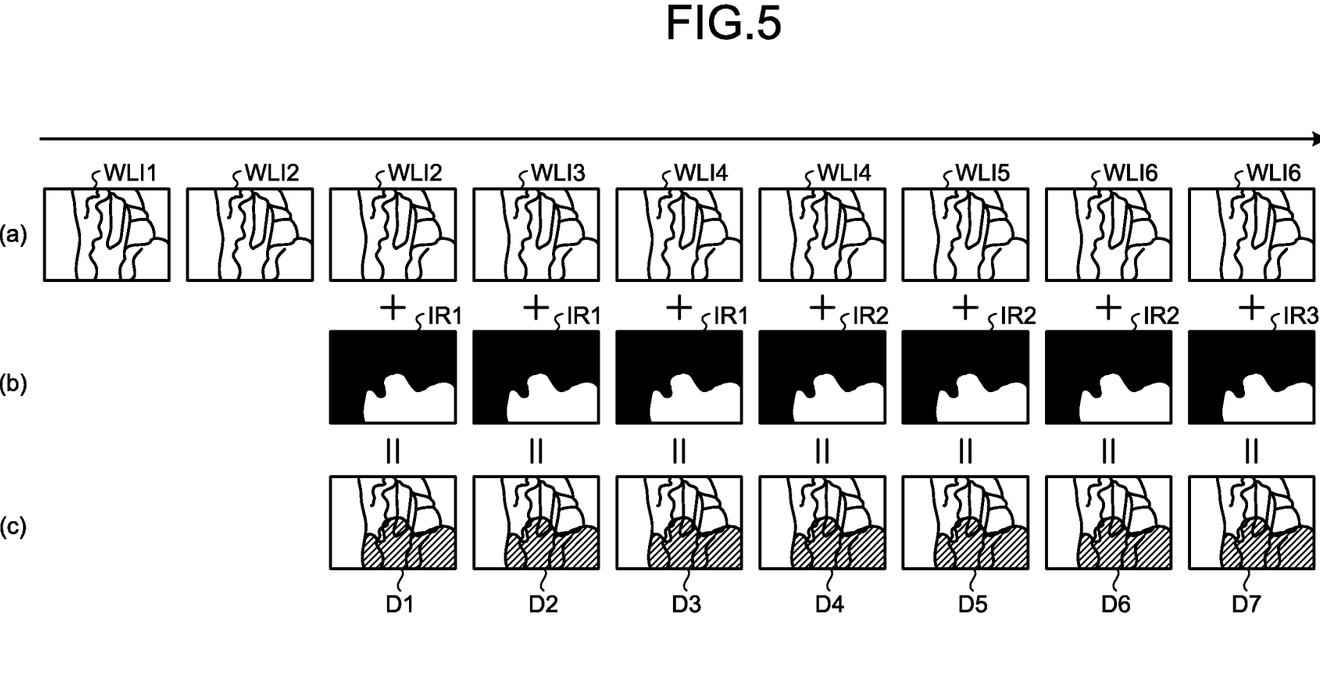
FIG. 5 is a diagram for describing the operation of the control device.

FIG. 3 is a flowchart illustrating the operation of the control device 9. FIGS. 4 and 5 are diagrams for describing the operation of the control device 9. Specifically, FIG. 4(*a*) is a time chart illustrating a synchronization signal. FIG. 4(*b*) is a time chart illustrating light emission timings of the first and second light sources 31 and 32. In FIG. 4(*b*), letters "WLI" are added in a period in which the first light source 31 emits light, and letters "IR" are added in a period in which the second light source 32 emits light. FIG. 4(*c*) is a time chart illustrating output timings of the captured image from the image sensor 521. FIGS. 4(*d*), 4(*h*), and 4(*l*) are time charts illustrating timings at which the subject picture image generated by the image sensor 521 is written to the memory 92. FIGS. 4 (*e*), 4(*i*), and 4(*m*) are time charts illustrating timings at which the subject picture image is read from the memory 92. In FIGS. 4(*d*), 4(*e*), 4(*h*), 4(*i*), 4(*l*), and 4(*m*), the respective subject picture images are illustrated as subject picture images WLI1 to WLI6 to discriminate between different captured timings. FIGS. 4(*f*), 4(*j*), and 4(*n*) are time charts illustrating timings at which the fluorescent picture image generated by the image sensor 521 is written in the memory 92. FIGS. 4(*g*), 4(*k*), and 4(*o*) are time charts illustrating timings at which the fluorescent picture image is read from the memory 92. In FIGS. 4(*f*), 4(*g*), 4(*j*), 4(*k*), 4(*n*), and 4(*o*), the respective fluorescent picture images are illustrated as fluorescent picture images IR1 to IR3 to discriminate between different captured timings. FIG. 5(*a*) is a diagram in which the subject picture images WLI1 to WLI6 that are sequentially input to the first image processor 932 are arranged in time series. FIG. 5(*b*) is a diagram in which the fluorescent picture images IR1 to IR3 that are sequentially input to the second image processor 933 are arranged in time series. In FIG. 5(*b*), in the fluorescent picture images IR1 to IR3, an excitation region excited by the fluorescent substance (drug) such as indocyanine green in the living body is expressed in white, and a region other than the excitation region is expressed in black. FIG. 5(*c*) is a diagram in which superimposed images D1 to D7 sequentially generated by the superimposed image generation unit 934 are arranged in time series. In FIG. 5(*c*), in the superimposed images D1 to D7, the above-described excitation region is represented by diagonal lines.

First, the light source controller 941 executes time-division driving of the first and second light sources 31 and 32 as described below (Step S1).

As illustrated in FIG. 4(*b*), the light source controller 941 causes the first light source 31 to perform pulse light emission in the first period T1 and causes the second light source 32 to perform pulse light emission in the second period T2 that is different from the first period T1 and is less frequent than the first period T1, among the respective periods T that are periodically repeated, on the basis of the synchronization signal (FIG. 4(a)).

In the present embodiment, as illustrated in FIG. 4(b), among the respective periods T that are periodically repeated, the period T0 that corresponds to the second period T2 is repeated after the first period T1 is consecutively repeated twice. That is, the frequency of the second period T2 is half that of the first period T1. In other words, a ratio between the first period T1 and the second period T2 is 2:1.

In FIG. 4(b), the pulse light emission of the first light source 31 starts at a timing ST at which the first period T1 starts, and the pulse light emission of the first light source 31 ends at a timing EN before the end of the first period T1, and the present disclosure is not limited thereto. For example, the pulse light emission of the first light source 31 may be continuously performed during the first period T1. Note that the same applies to the pulse light emission of the second light source 32.

After Step S1, the imaging controller 942 causes the image sensor 521 to capture each of the subject image and the fluorescent image in each period T in synchronization with the light emission timings of the first and second light sources 31 and 32 on the basis of the synchronization signal (FIG. 4(a)) (Steps S2 to S4). That is, when in the first period T1 (Step S2: Yes), in other words, when the inside of the living body is irradiated with white light, the image sensor 521 captures the subject image reflected in the living body to generate the subject picture image (Step S3). On the other hand, when in the second period T2 (Step S2: No), in other words, when the inside of the living body is irradiated with near-infrared excitation light, the image sensor 521 generates the fluorescent picture image by capturing the fluorescent image emitted from the inside of the living body as the fluorescent substance (drug) such as indocyanine green or the like in the living body is excited (Step S4).

After Step S3 and Step S4, the memory controller 931 controls writing and reading of the captured image to and from the memory 92 as described below on the basis of the synchronization signal (FIG. 4(a)) (Step S5).

In the following description (Steps S5 to S8), only processing of the subject picture images WLI1 to WLI6 captured in first periods T11 to T16, respectively, and the fluorescent picture images IR1 to IR3 captured in second periods T21 to T23, respectively, will be described for convenience of explanation. A description of processing of the subject picture image and the fluorescent picture image captured after the second period T23 will be omitted.

The memory controller 931 writes the subject picture image WLI1 captured in the earliest first period T11 in FIG. 4(b) to the memory 92 at a first write timing W1 (FIG. 4(d)) which is substantially the same timing as an output timing (FIG. 4(c)) of the subject picture image WLI1 from the image sensor 521. Further, the memory controller 931 writes the subject picture image WLI2 captured in the first period T12 (FIG. 4(b)) immediately after the first period T11 to the memory 92 at a second write timing W2 (FIG. 4(d)) which is substantially the same timing as an output timing (FIG. 4(c)) of the subject picture image WLI2 from the image sensor 521.

Further, the memory controller 931 reads the subject picture image WLI1 from the memory 92 at a first read timing R1 (FIG. 4(e)) which is substantially the same timing as a timing at which the writing of the subject picture image WLI2 to the memory 92 is completed, and inputs the read subject picture image WLI1 to the first image processor 932. Further, the memory controller 931 reads the subject picture image WLI2 from the memory 92 at a second read timing R2 (FIG. 4(e)) which is substantially the same timing as a timing at which the reading of the subject picture image WLI1 from the memory 92 is completed, and inputs the read subject picture image WLI2 to the first image processor 932. In addition, the memory controller 931 reads the subject picture image WLI2 from the memory 92 again at a third read timing R3 (FIG. 4(e)) which is substantially the same timing as a timing at which the reading of the subject picture image WLI2 from the memory 92 is completed, and inputs the subject picture image WLI2 that is read again to the first image processor 932, to artificially generate the subject picture image captured in the second period T21 (FIG. 4(b)) immediately after the first period T12.

Hereinafter, for convenience of explanation, the subject picture image WLI2 read from the memory 92 at the second read timing R2 is referred to as a first subject picture image WLI2. Further, the subject picture image WLI2 read from the memory 92 again at the third read timing R3 is referred to as a second subject picture image WLI2.

In addition, the memory controller 931 writes the fluorescent picture image IR1 captured in the second period T21 to the memory 92 at a third write timing W3 (FIG. 4(f)) which is substantially the same timing as an output timing (FIG. 4(c)) of the fluorescent picture image IR1 from the image sensor 521. Further, the memory controller 931 reads the fluorescent picture image IR1 from the memory 92 at the third read timing R3, and inputs the read fluorescent picture image IR1 to the second image processor 933. In addition, the memory controller 931 reads the fluorescent picture image IR1 from the memory 92 again at a fourth read timing R4 (FIG. 4(g)) which is substantially the same timing as a timing at which the reading of the fluorescent picture image IR1 from the memory 92 is completed, and inputs the fluorescent picture image IR1 that is read again to the second image processor 933, to artificially generate the fluorescent picture image captured in the first period T13 (FIG. 4(b)) immediately after the second period T21. Furthermore, the memory controller 931 reads the fluorescent picture image IR1 from the memory 92 again (the third time) at a fifth read timing R5 (FIG. 4(g)) which is substantially the same timing as a timing at which the reading of the fluorescent picture image IR1 from the memory 92 performed for the second time is completed, and inputs the fluorescent picture image IR1 that is read again to the second image processor 933, to artificially generate the fluorescent picture image captured in the first period T14 (FIG. 4(b)) immediately after the first period T13.

Hereinafter, for convenience of explanation, the fluorescent picture image IR1 read from the memory 92 at the third read timing R3 is referred to as a first fluorescent picture image IR1. In addition, the fluorescent picture image IR1 read from the memory 92 again (the second time) at the fourth read timing R4 is referred to as a second fluorescent picture image IR1. In addition, the fluorescent picture image IR1 read from the memory 92 again (the third time) at the fifth read timing R5 is referred to as a third fluorescent picture image IR1.

Further, the memory controller 931 writes the subject picture image WLI3 captured in the first period T13 to the memory 92 at a fourth write timing W4 (FIG. 4(h)) which is substantially the same timing as an output timing (FIG. 4(c)) of the subject picture image WLI3 from the image sensor 521. Further, the memory controller 931 writes the subject picture image WLI4 captured in the first period T14 to the memory 92 at a fifth write timing W5 (FIG. 4(h)) which is substantially the same timing as an output timing (FIG. 4(c)) of the subject picture image WLI4 from the image sensor 521.

Further, the memory controller 931 reads the subject picture image WLI3 from the memory 92 at the fourth read timing R4 which is substantially the same timing as a timing at which the writing of the subject picture image WLI4 to the memory 92 is completed, and inputs the read subject picture image WLI3 to the first image processor 932. Further, the memory controller 931 reads the subject picture image WLI4 from the memory 92 at the fifth read timing R5 which is substantially the same timing as a timing at which the reading of the subject picture image WLI3 from the memory 92 is completed, and inputs the read subject picture image WLI4 to the first image processor 932. In addition, the memory controller 931 reads the subject picture image WLI4 from the memory 92 again at a sixth read timing R6 (FIG. 4(i)) which is substantially the same timing as a timing at which the reading of the subject picture image WLI4 from the memory 92 is completed, and inputs the subject picture image WLI4 that is read again to the first image processor 932, to artificially generate the subject picture image captured in the second period T22 (FIG. 4(b)) immediately after the first period T14.

Hereinafter, for convenience of explanation, the subject picture image WLI4 read from the memory 92 at the fifth read timing R5 is referred to as a first subject picture image WLI4. Further, the subject picture image WLI4 read from the memory 92 again at the sixth read timing R6 is referred to as a second subject picture image WLI4.

In addition, the memory controller 931 writes the fluorescent picture image IR2 captured in the second period T22 to the memory 92 at a sixth write timing W6 (FIG. 4(j)) which is substantially the same timing as an output timing (FIG. 4(c)) of the fluorescent picture image IR2 from the image sensor 521. Further, the memory controller 931 reads the fluorescent picture image IR2 from the memory 92 at the sixth read timing R6, and inputs the read fluorescent picture image IR2 to the second image processor 933. In addition, the memory controller 931 reads the fluorescent picture image IR2 from the memory 92 again at a seventh read timing R7 (FIG. 4(k)) which is substantially the same timing as a timing at which the reading of the fluorescent picture image IR2 from the memory 92 is completed, and inputs the fluorescent picture image IR2 that is read again to the second image processor 933, to artificially generate the fluorescent picture image captured in the first period T15 (FIG. 4(b)) immediately after the second period T22. Furthermore, the memory controller 931 reads the fluorescent picture image IR2 from the memory 92 again (the third time) at an eighth read timing R8 (FIG. 4(k)) which is substantially the same timing as a timing at which the reading of the fluorescent picture image IR2 from the memory 92 performed for the second time is completed, and inputs the fluorescent picture image IR2 that is read again to the second image processor 933, to artificially generate the fluorescent picture image captured in the first period T16 (FIG. 4(b)) immediately after the first period T15.

Hereinafter, for convenience of explanation, the fluorescent picture image IR2 read from the memory 92 at the sixth read timing R6 is referred to as a first fluorescent picture image IR2. In addition, the fluorescent picture image IR2 read from the memory 92 again (the second time) at the seventh read timing R7 is referred to as a second fluorescent picture image IR2. In addition, the fluorescent picture image IR2 read from the memory 92 again (the third time) at the eighth read timing R8 is referred to as a third fluorescent picture image IR2.

Further, the memory controller 931 writes the subject picture image WLI5 captured in the first period T15 to the memory 92 at a seventh write timing W7 (FIG. 4(l)) which is substantially the same timing as an output timing (FIG. 4(c)) of the subject picture image WLI5 from the image sensor 521. Further, the memory controller 931 writes the subject picture image WLI6 captured in the first period T16 to the memory 92 at an eighth write timing W8 (FIG. 4(m)) which is substantially the same timing as an output timing (FIG. 4(c)) of the subject picture image WLI6 from the image sensor 521.

Further, the memory controller 931 reads the subject picture image WLI5 from the memory 92 at the seventh read timing R7 which is substantially the same timing as a timing at which the writing of the subject picture image WLI6 to the memory 92 is completed, and inputs the read subject picture image WLI5 to the first image processor 932. Further, the memory controller 931 reads the subject picture image WLI6 from the memory 92 at the eighth read timing R8 which is substantially the same timing as a timing at which the reading of the subject picture image WLI5 from the memory 92 is completed, and inputs the read subject picture image WLI6 to the first image processor 932. In addition, the memory controller 931 reads the subject picture image WLI6 from the memory 92 again at a ninth read timing R9 (FIG. 4(m)) which is substantially the same timing as a timing at which the reading of the subject picture image WLI6 from the memory 92 is completed, and inputs the subject picture image WLI6 that is read again to the first image processor 932, to artificially generate the subject picture image captured in the second period T23 (FIG. 4(b)) immediately after the first period T16.

Hereinafter, for convenience of explanation, the subject picture image WLI6 read from the memory 92 at the eighth read timing R8 is referred to as a first subject picture image WLI6. Further, the subject picture image WLI6 read from the memory 92 again at the ninth read timing R9 is referred to as a second subject picture image WLI6.

In addition, the memory controller 931 writes the fluorescent picture image IR3 captured in the second period T23 to the memory 92 at a ninth write timing W9 (FIG. 4(n)) which is substantially the same timing as an output timing (FIG. 4(c)) of the fluorescent picture image IR3 from the image sensor 521. Further, the memory controller 931 reads the fluorescent picture image IR3 from the memory 92 at the ninth read timing R9, and inputs the read fluorescent picture image IR3 to the second image processor 933. In addition, the memory controller 931 reads the fluorescent picture image IR3 from the memory 92 again at a tenth read timing R10 (FIG. 4(o)) which is substantially the same timing as a timing at which the reading of the fluorescent picture image IR3 from the memory 92 is completed, and inputs the fluorescent picture image IR3 that is read again to the second image processor 933, to artificially generate the fluorescent picture image captured in the first period T17 (FIG. 4(b)) immediately after the second period T23. Furthermore, the memory controller 931 reads the fluorescent picture image IR3 from the memory 92 again (the third time) at an eleventh read timing R11 (FIG. 4(o)) which is substantially the same timing as a timing at which the reading of the fluorescent picture image IR3 from the memory 92 performed for the second time is completed, and inputs the fluorescent picture image IR3 that is read again to the second image processor 933, to artificially generate the fluorescent picture image captured in the first period T18 (FIG. 4(b)) immediately after the first period T17.

Hereinafter, for convenience of explanation, the fluorescent picture image IR3 read from the memory 92 at the ninth read timing R9 is referred to as a first fluorescent picture image IR3. In addition, the fluorescent picture image IR3 read from the memory 92 again (the second time) at the tenth read timing R10 is referred to as a second fluorescent picture image IR3. In addition, the fluorescent picture image IR3 read from the memory 92 again (the third time) at the eleventh read timing R11 is referred to as a third fluorescent picture image IR3.

In summary, the subject picture images WLI1 to WLI6 are input to the first image processor 932 in the order of the subject picture image WLI1, the first subject picture image WLI2, the second subject picture image WLI2, the subject picture image WLI3, the first subject picture image WLI4, the second subject picture image WLI4, the subject picture image WLI5, the first subject picture image WLI6, and the second subject picture image WLI6 as illustrated in FIG. 5(a). Further, the fluorescent picture images IR1 to IR3 are input to the second image processor 933 in the order of the first fluorescent picture image IR1, the second fluorescent picture image IR1, the third fluorescent picture image IR1, the first fluorescent picture image IR2, the second fluorescent picture image IR2, the third fluorescent picture image IR2, and the first fluorescent picture image IR3 as illustrated in FIG. 5(b).

After Step S5, the first and second image processors 932 and 933 perform the following processing (Step S6).

That is, the first image processor 932 sequentially performs the first image processing on the sequentially input subject picture images WLI1 to WLI6. Further, the second image processor 933 sequentially performs the second image processing on the sequentially input fluorescent picture images IR1 to IR3.

After Step S6, the superimposed image generation unit 934 performs the following processing (Step S7).

That is, the superimposed image generation unit 934 generates a superimposed image D1 by superimposing corresponding pixels in entire regions of the second subject picture image WLI2 subjected to the first image processing, and the first fluorescent picture image IR1 subjected to the second image processing as illustrated in FIG. 5(c), the second subject picture image WLI2 and the first fluorescent picture image IR1 being read from the memory 92, at the same third read timing R3. Similarly, the superimposed image generation unit 934 sequentially generates a superimposed image D2 based on the subject picture image WLI3 and the second fluorescent picture image IR1, a superimposed image D3 based on the first subject picture image WLI4 and the third fluorescent picture image IR1, a superimposed image D4 based on the second subject picture image WLI4 and the first fluorescent picture image IR2, a superimposed image D5 based on the subject picture image WLI5 and the second fluorescent picture image IR2, a superimposed image D6 based on the first subject picture image WLI6 and the third fluorescent picture image IR2, and a superimposed image D7 based on the second subject picture image WLI6 and the first fluorescent picture image IR3.

After Step S7, the display controller 935 sequentially generates video signals based on the superimposed images D1 to D7 sequentially generated by the superimposed image generation unit 934, and sequentially outputs the video signals to the display device 7 (Step S8). Accordingly, the superimposed images D1 to D7 are sequentially displayed on the display device 7.

According to the present embodiment described above, the following effects may be obtained.

In the medical light source apparatus 100 according to the present embodiment, the first light source 31 is an LED that emits white light. On the other hand, the second light source 32 is a semiconductor laser that emits near-infrared excitation light. That is, according to specifications of the first and second light sources 31 and 32, the first light source 31 has a longer lifetime than that of the second light source 32. Further, in the medical light source apparatus 100, the light source controller 941 controls the operations of the first and second light sources 31 and 32 in a state in which the pulse light emission of the second light source 32 is less frequent than the pulse light emission of the first light source 31.

Therefore, the second light source 32 with a short lifetime may be used for a shorter time as compared with the first light source 31 with a long lifetime to reduce the lifetime difference between the first and second light sources 31 and 32. As a result, in the medical light source apparatus 100 according to the present embodiment, the first and second light sources 31 and 32 may be replaced in substantially the same period, thereby making it possible to improve convenience.

In the medical observation system 1 according to the present embodiment, the light source controller 941 causes the first light source 31 to perform pulse light emission in the first period T1, and causes the second light source 32 to perform pulse light emission in the second period T2. Further, the image sensor 521 generates the subject picture images WLI1 to WLI6 by capturing images in the first period T1, and generates the fluorescent picture images IR1 to IR3 by capturing images in the second period T2. The subject picture images WLI1 to WLI6 are input to the first image processor 932. Meanwhile, the fluorescent picture images IR1 to IR3 are input to the second image processor 933.

Therefore, the first image processing may be performed on the subject picture images WLI1 to WLI6, and the second image processing different from the first image processing may be performed on the fluorescent picture images IR1 to IR3. That is, appropriate image processing may be performed according to characteristics of the subject image and the fluorescent image, and appropriate superimposed images D1 to D7 may be displayed on the display device 7.

Further, in the medical observation system 1 according to the present embodiment, the memory controller 931 reads the subject picture image that is immediately previously read from the memory 92, again from the memory 92, and inputs the subject picture image that is read again to the first image processor 932, to artificially generate the subject picture image captured in the second period T2. Similarly, the memory controller 931 reads the fluorescent picture image that is immediately previously read from the memory 92, again from the memory 92, and inputs the fluorescent picture image that is read again to the second image processor 933, to artificially generate the fluorescent picture image captured in the first period T1. A ratio between the first period T1 and the second period T2 is 2:1.

Here, it is assumed that the memory controller 931 performs the same processing as described above when the first period T1 and the second period T2 are 1:1. Further, it is assumed that a frame rate of the image sensor 521 is 60 fps. In this case, the subject picture image captured at 60 fps is displayed twice in succession and the display is repeated, such that a frame rate of the subject picture image is 30 fps. Note that the same applies to the fluorescent picture image. That is, since the frame rates of both of the subject picture image and the fluorescent picture image are relatively low (30 fps), it is difficult for both images to move smoothly and it is difficult to improve display quality.

Meanwhile, in a case of the configuration according to the present embodiment, two of the three subject picture images arranged in time series are the same image, and thus the frame rate of the subject picture image is 40 fps. Further, since the three fluorescent picture images arranged in time series are the same image, the frame rate of the fluorescent picture image is 20 fps. That is, among the subject picture image and the fluorescent picture image, the frame rate of the subject picture image based on which a smoothness of a motion of a video may be easily determined may be relatively high, and thus the display quality may be improved.

Other Embodiments

Hereinabove, the embodiment for carrying out the present disclosure has been described, but the present disclosure should not be limited only to the embodiment described above.

In the above-described embodiment, the first light source 31 emits white light and the second light source 32 emits near-infrared excitation light. However, the present disclosure is not limited thereto. The first and second light sources 31 and 32 may have other configurations as long as the first light source 31 emits light in the first wavelength range, and the second light source 32 emits light in the second wavelength range different from the first wavelength range. Here, the first and second wavelength ranges may be partially overlapping bands or may not overlap each other at all.

In the related art, photodynamic diagnosis (PDD), which is one of cancer diagnostic methods for detecting cancer cells, has been known.

In the photodynamic diagnosis, for example, a photosensitive substance such as 5-aminolevulinic acid (hereinafter, referred to as 5-ALA) is used. The 5-ALA is a natural amino acid originally contained in a living body of an animal and a plant. The 5-ALA is incorporated into cells after administration into the body and is biosynthesized into protoporphyrin in mitochondria. In cancer cells, the protoporphyrin is accumulated excessively. Protoporphyrin that is excessively accumulated in the cancer cells has photoactivity. Therefore, when the protoporphyrin is excited by excitation light (for example, blue visible light in a wavelength range of 375 nm to 445 nm), the protoporphyrin emits fluorescent light (for example, red fluorescent light in a wavelength range of 600 nm to 740 nm). As described above, the cancer diagnostic method in which a photosensitive substance is used to make cancer cells emit fluorescent light is called photodynamic diagnosis.

Further, in the above-described embodiment, the first light source 31 may be implemented by an LED that emits white light and the second light source 32 may be implemented by a semiconductor laser that emits excitation light (for example, blue visible light in a wavelength range of 375 nm to 445 nm) that excites protoporphyrin. Even in the case of the configuration described above, the same effects as those of the above-described embodiment may be obtained.

In the above-described embodiment, the first and second light sources 31 and 32 are driven in a time division manner (each emits light in different time periods), but the present disclosure is not limited thereto and a configuration in which the first and second light sources 31 and 32 perform pulse light emission in the same time period may also be employed as long as the pulse light emission of the second light source 32 is less frequent than the pulse light emission of the first light source 31. Further, a ratio between the frequency of the pulse light emission of the first light source 31 and the frequency of the pulse light emission of the second light source 32 is not limited to 2:1, and any ratio may be adopted as long as the pulse light emission of the second light source 32 is less frequent than the pulse light emission of the first light source 31.

In the above-described embodiment, for example, a configuration in which one of the two light sources may be selected to perform pulse light emission less frequently or more frequently than the other by operating the input unit 95.

In the above-described embodiment, the subject picture image and the fluorescent picture image are superimposed, but the present disclosure is not limited thereto, and the subject picture image and the fluorescent picture image may be displayed on different screens on the display device 7, respectively, by a picture-in-picture (PinP) operation or the like. Further, a configuration in which a plurality of display devices 7 are provided and the subject picture image and the fluorescent picture image are displayed on different display devices 7, respectively, may be employed.

In the above-described embodiment, the medical light source apparatus according to the present disclosure is mounted on the medical observation system 1 in which the insertion unit 2 is implemented by a rigid endoscope. However, the present disclosure is not limited thereto. For example, the medical light source apparatus according to the present disclosure may be mounted on a medical observation system in which the insertion unit 2 is implemented by a flexible endoscope. Further, the medical light source apparatus according to the present disclosure may be mounted on a medical observation system such as a surgical microscope (for example, see JP 2016-42981 A) for magnifying and observing a predetermined visual field region in a subject (in vivo) or a surface of the subject (a surface of a living body).

In the above-described embodiment, some components of the camera head 5 and some components of the control device 9 may be provided in, for example, the connector CN1 or the connector CN2.

The medical light source apparatus and the medical observation system according to the present disclosure may improve convenience.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:
1. A medical observation system comprising:
 a first light source configured to emit light in a first wavelength range;
 a second light source configured to emit light in a second wavelength range different from the first wavelength range;
 processing circuitry configured to control the first light source and the second light source to perform pulse light emission in a state in which the pulse light emission of the second light source is less frequent than the pulse light emission of the first light source;
 an imaging device configured to capture an image of an observation target irradiated with light from the first light source and the second light source; and
 a memory configured to store data regarding the captured image, wherein the processing circuitry is further configured to
control writing and reading of the data to and from the memory,
superimpose a first image of the observation target irradiated with first light from the second light source with a second image of the observation target irradiated with second light from the first light source, and
superimpose the first image with a third image of the observation target irradiated with third light from the first light source, the second light and the third light being irradiated from the first light source at different time.

2. The medical observation system according to claim 1, wherein the processing circuitry is configured to control the first light source and the second light source to perform the pulse light emission in a first period and a second period, respectively, among periods that are periodically repeated, the second period being different from the first period and being less frequent than the first period.

3. The medical observation system according to claim 1, wherein
the first light source is configured to emit white light, and
the second light source is configured to emit excitation light that excites a fluorescent substance.

4. The medical observation system according to claim 3, wherein
the first light source is a light emitting diode (LED), and
the second light source is a semiconductor laser.

5. The medical observation system according to claim 1, wherein
the processing circuitry is configured to control the first light source and the second light source to perform the pulse light emission in the first period and the second period, respectively, among the respective periods that are periodically repeated, the second period being different from the first period and being less frequent than the first period,
the imaging device includes only one image sensor configured to generate a captured image by capturing, and
the image sensor is configured to:
generate a first captured image by capturing an image of the observation target in the first period; and
generate a second captured image by capturing an image of the observation target in the second period.

6. The medical observation system according to claim 5, wherein
the processing circuitry is configured to:
process the first captured image and the second captured image sequentially generated by the imaging device by performing first image processing on the first captured image, and
performing second image processing different from the first image processing on the second captured image.

7. The medical observation system according to claim 6, wherein the processing circuitry is configured to:
sequentially write the first captured image and the second captured image sequentially generated by the imaging device to the memory,
input the first captured image read from the memory to the first image processor, and
input the second captured image read from the memory to the second image processor.

8. The medical observation system according to claim 7, wherein the processing circuitry is configured to read the first captured image that is immediately previously read from the memory, again from the memory, and input the first captured image that is read again to the first image processor, to artificially generate the first captured image captured in the second period.

9. The medical observation system according to claim 7, wherein the processing circuitry is configured to read the second captured image that is immediately previously read from the memory, again from the memory, and input the second captured image that is read again to the second image processor, to artificially generate the second captured image captured in the first period.

* * * * *